(12) United States Patent
Zhao et al.

(10) Patent No.: US 6,586,618 B1
(45) Date of Patent: Jul. 1, 2003

(54) CC-1065 ANALOG SYNTHESIS

(75) Inventors: Robert Yongxin Zhao, Watertown, MA (US); Ravi V. J. Chari, Newton, MA (US)

(73) Assignee: Immunogen Inc., Cambridge, MA (US)

( * ) Notice: Subject to any disclaimer, the term of this patent is extended or adjusted under 35 U.S.C. 154(b) by 0 days.

(21) Appl. No.: 10/265,329

(22) Filed: Oct. 7, 2002

Related U.S. Application Data

(62) Division of application No. 10/116,052, filed on Apr. 5, 2002.

(51) Int. Cl.$^7$ ............................................... C07C 69/76
(52) U.S. Cl. ........................ 560/100; 556/420; 564/149
(58) Field of Search ........................ 564/149; 560/100; 556/420

(56) References Cited

PUBLICATIONS

Boger et al, J. Org. Chem. 1997, 62 (25), 8875–8891.*
Boger et al, "CC–1065 and the Duocarmycins: Synthetic Studies", *Chem. Rev.*, 97:787–828 (1997).

* cited by examiner

Primary Examiner—Joseph K. McKane
Assistant Examiner—Kamal Saeed
(74) Attorney, Agent, or Firm—Sughrue Mion, PLLC

(57) ABSTRACT

Improved synthesis of seco(–)CBI (5-hydroxy-3-amino-1-[S]-(chloromethyl)-1,2-dihydro-3H-benz(e)indole):

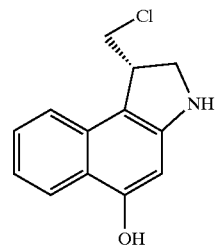

and improved syntheses therefrom of a wide variety of CC-1065 analogs that comprise a cyclopropabenzidole (CBI) alkylating moiety, and which are collectively DC1 and its derivatives, for the synthesis of cell-targeted therapeutic agents.

2 Claims, 3 Drawing Sheets

CC-1065 ANALOG SYNTHESIS

This application is a Divisional of U.S. application Ser. No. 10/116,052, filed Apr. 5, 2002 (now allowed). The disclosure of which is incorporated herein by reference.

FIELD OF THE INVENTION

The present invention relates to the synthesis of cytotoxic anti-tumor antibiotics such as CC-1065 and analogs thereof. In particular, the present invention provides an improved synthesis for seco(−)CBI (5-hydroxy-3-amino-1-[S]-(chloromethyl)-1,2-dihydro-3H-benz(e)indole), and for the synthesis therefrom of CC-1065 analogs comprising a cyclopropabenzindole (CBI) alkylating moiety, which may be incorporated into cell-targeted therapeutic agents.

BACKGROUND

CC-1065 is a highly cytotoxic anti-tumor antibiotic isolated from cultures of *Streptomyces zelensis*. The CC-1065 molecule consists of three substituted pyrroloindole subunits linked by amide bonds. The "A" subunit is the alkylating cyclopropapyrroloindole (CPI) moiety, while the "B" and "C" subunits are identical pyrroloindole moieties.

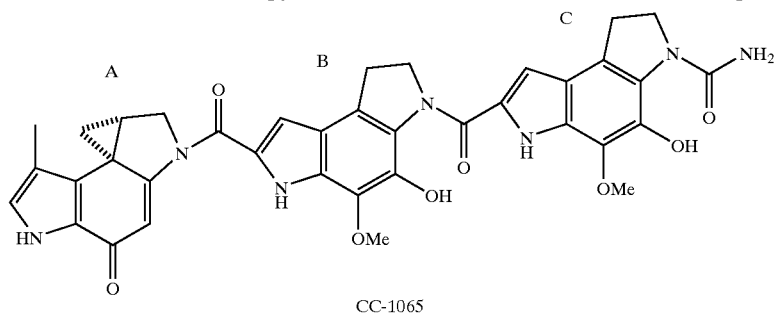

CC-1065

Novel cytotoxic agent-cell binding agent conjugates comprising a cell-binding agent chemically linked to analogs of CC-1065 have been described [U.S. Pat. Nos. 5,475,092; 5,585,499; 5,846,545, R. V. J. Chari et al., *Cancer Res.*, 55, 4079–4084 (1995)]. These cytotoxic agent-cell binding agent conjugates have therapeutic use because they deliver the cytotoxic agent to a specific cell population in a targeted fashion. In these cytotoxic agents, herein called DC1 and its derivatives, the alkylating CPI subunit "A" was replaced by the benzannelated analog cyclopropabenzindole (CBI).

The CBI unit can exist in the ring-closed cyclopropyl form or in the ring-open seco (chloromethyl) form. The "B" and "C" subunits were replaced with indole units. In addition, the terminal indole unit bears a substituent that allowed for linkage to cell-binding agents.

CBI is the precursor required for the synthesis of DC1 drugs and its derivatives. The original synthesis of CBI was described by D. L. Boger et al., [*J Org. Chem.*, 55, 5823–5833 (1990)]. An "improved" synthesis, also described by D. L. Boger et al., [*J. Org. Chem.*, 57, 2873–2876 (1992)] is a 15-step process starting from naphthalene diol. Other pathways for the syntheses of CBI from different starting materials have also been described [K. J. Drost & M. P. Cava, *J. Org. Chem.*, 56, 2240–2244 (1991), P. A. Aristoff & P. D. Johnson, *J. Org. Chem.*, 57, 6234–6239 (1992)]. These syntheses are lengthy, time-consuming, expensive and provide poor yields.

A key step in the synthesis of CBI is the resolution of the enantiomers at the seco-CBI stage. Only the seco(−) enantiomer is biologically active, and it is important to efficiently remove the inactive (+) isomer. Isomer separation can be achieved, for example, by chiral HPLC. This method is not very efficient when applied to seco-CBI because the separation between the two enantiomers is poor. In addition, even the optimized separation on a chiral column is poor (retention time difference between the two isomers is less than 5 minutes), and requires a very non-polar solvent system, such as a mixture of 95% hexane and 5% isopropanol (Boger et al., 116, J. Am. Chem Soc., 7996–8006 (1994). Under these conditions, seco-CBI is poorly soluble, resulting in low efficiency (small loading amounts) on the column, and thus, long processing times. Alternatively, the enantiomeric mixture can be converted into a set of diastereomers by esterification with a chiral acid, such as mandelic acid, followed by separation by HPLC. However, the separated ester has to be hydrolyzed and then repurified, thus adding an extra processing step.

The therapeutic utility and promise of drugs such as DC1 and its derivatives, for example in the treatment of various

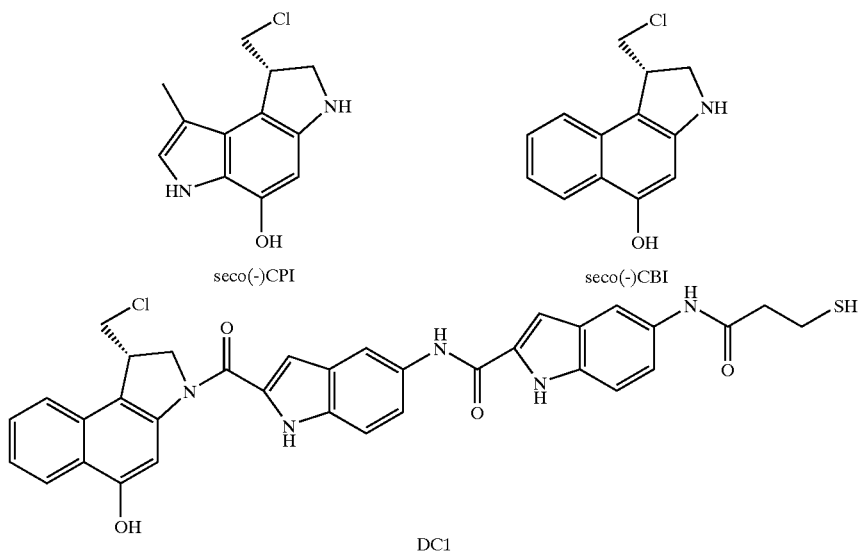

cancers, makes it desirable that improved synthetic methods be developed in order to be able to manufacture CBI in large scale, by a simple, easily scalable, high-yield, inexpensive process that uses inexpensive and easily available starting materials.

The present invention provides such an improved synthetic method that addresses the aforementioned shortcomings of the prior art. All these advantages and more are provided by the invention described herein, as will be apparent to one of skill in the art upon reading the following disclosure and examples.

SUMMARY OF THE INVENTION

The inventors have discovered a new, economical and efficient synthesis for seco(-)CBI that can utilize, for example, the commercially available and inexpensive compound 1,3-dihydroxynaphthalene as a starting material, and which can be accomplished in as few as seven steps.

The inventors have further provided related flexible and efficient syntheses for the conversion of seco(-)CBI into a wide variety of DC1 drugs. While there are several differences between the synthetic scheme for seco(-)CBI described herein and any previously reported method, one exemplary difference is the use of the same protecting group for the amino and the hydroxy groups of the key precursor, 4-hydroxy-2-naphthyl amine. Thus, in one embodiment of the method described herein, a di-tert.-butyloxycarbonyl (di-t-boc) protected compound is used, instead of a separate benzyl protecting group for the hydroxyl group and a tert.-butyloxycarbonyl (t-boc) protecting group for the amine function, described previously. Thus, in the present syntheses, some of the redundant protection and deprotection steps have been removed. These and other changes have shortened the synthesis time, improved the product yield considerably, and also improved the separation of enantiomers.

In the present invention, the use of two t-boc protecting groups is preferred and gives a seco-CBI enantiomeric mixture that separates well on a chiral HPLC column. In addition, the column can be run with a solvent mixture with a higher polarity, for example containing 20% isopropanol, in which the compound has good solubility. These two features greatly increase the loading capacity of the column and therefore the efficiency of the separation process, and thus decrease the processing time considerably.

Thus, in a first aspect, the present invention provides a process for preparing the seco(-)CBI of formula (I):

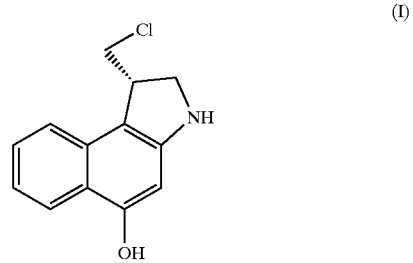

(I)

in which a di-protected compound of formula (II) is used, in which R is a protecting group such that the amino group and hydroxyl group are protected by the same compound:

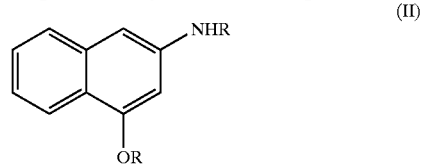

(II)

and the compound of formula (II) is converted by alkylation and ring-closure reactions to provide a racemic mixture represented by a compound of formula (III):

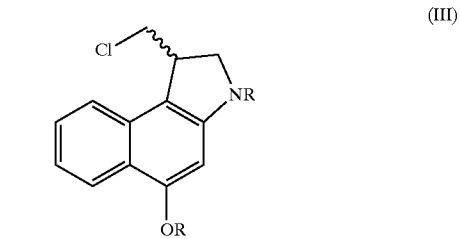

(III)

The (-) isomer of racemate (III) can be isolated, for example by chiral chromatography, and the isolated (-) isomer of the compound of formula (III) is deprotected to produce the compound of formula (I).

In preferred embodiments, R is tert-butyloxycarbonyl and the alkylation step employs 1,3-dichloropropene.

In certain embodiments, a compound of formula (II) can be conveniently prepared from an inexpensive and easily obtained starting material such as 1,3-dihydroxynapthalene by amination and protection of the hydroxyl and amine groups (FIG. 1).

In a second aspect, the present invention provides a process for preparing DC1 by reacting the amino group of a compound of the seco(-)CBI of formula (I) to form a peptide bond, where the seco(-)CBI may be prepared according to the method of the present invention.

Thus, in a first embodiment of this second aspect of the invention, a peptide bond is formed by reacting the amino group of seco(-)CBI with the carboxyl group of, for example, a compound of formula (IV) under suitable conditions,

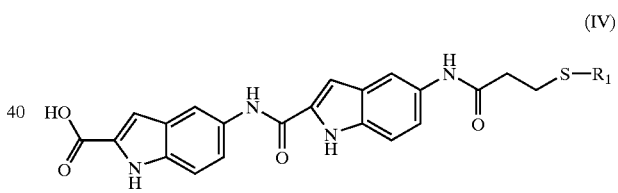

(IV)

in which $R_1$ represents, in this embodiment, an alkyl or aryl thio group that forms a disulfide bond within a compound of formula (IV), such as, for example, an alkyl or aryl thiol, or, more specifically, —S—$CH_3$ or —S-pyridyl. Such disulfides can be used to link the DC1 compound to, for example, a cell-targeting agent via a bond that can be cleaved inside the target cell.

This embodiment is not limited to only the synthesis of the DC1 compound corresponding to the product of the reaction using compound (IV), but can also be readily adapted to produce a wide variety of DC1 compounds, including those in which the group that is capable of bonding to a cell-targeting agent can be other than a thio or disulfide group, such as, for example, an acid-labile group, a photo-labile group, a peptidase-labile group, or an esteraselabile group, depending upon the analog of compound (IV) that is selected.

In a further embodiment of this aspect of the invention, it is not required that the coupling of seco(-)CBI occurs as a terminal step of the synthesis. Thus, in this embodiment the DC1 compound is synthesized from a bis-indolyl moiety, a disulfide-containing moiety, and seco(-)CBI, by their attachment via peptide bonds, and the order in which these three components of DC1 are assembled is not critical. For example, the bis-indolyl moiety and seco(–)CBI can be linked prior to the attachment of the disulfide-containing moiety.

DETAILED DESCRIPTION

Figure 1:
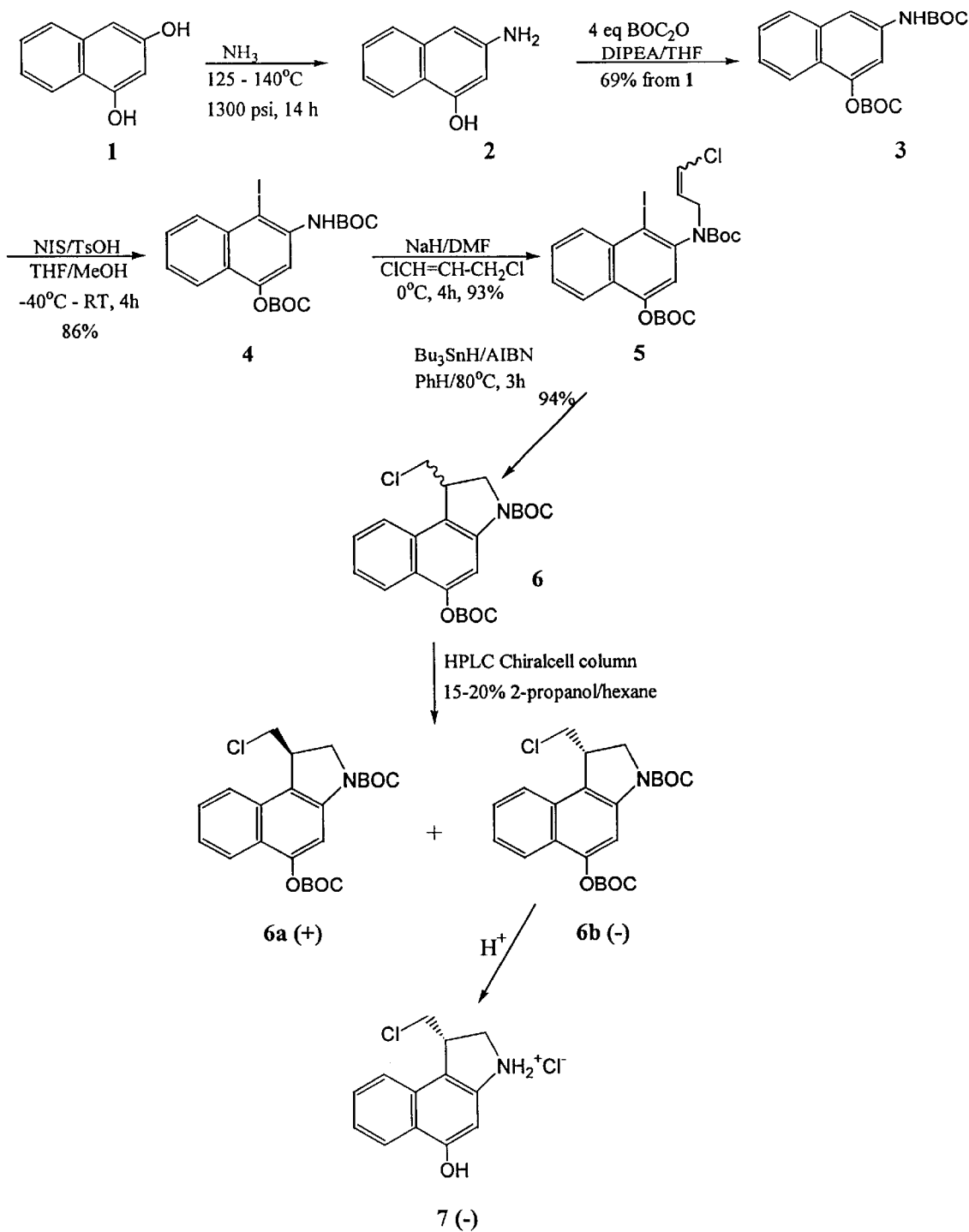
FIG. 1 illustrates a synthesis of seco(–)CBI (5-hydroxy-3-amino-1-[S]-(chloromethyl)-1,2-dihydro-3H-benz(e)indole) according to the method of the present invention.

The present invention provides an improved synthesis of seco(–)CBI (5-hydroxy-3-amino-1-[S]-(chloromethyl)-1,2-dihydro-3H-benz(e)indole) (7), and also improved syntheses of DC1 and its derivative compounds that use seco(–)CBI as a reagent.

Optionally, the synthesis of seco(–)CBI can utilize 1,3-dihydroxynapthalene as a starting material, which is inexpensive and readily available.

The present invention also provides novel compounds of formula (II):

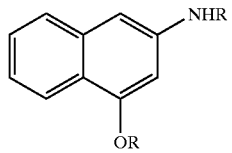

(II)

wherein R is a protecting group as defined herein.

The term "DC1 and its derivatives" as used herein refers to CC-1065 analogs having, as their alkylating subunit "A," a cyclopropabenzidole (CBI) subunit in its open chloromethyl form in place of the cyclopropapyrroloindole (CPI) unit of CC-1065. DC1 compounds further comprise "B" and "C" subunits that are indole units or analogs thereof. The "B" and "C" subunits are linked by an amide bond, and provide carboxyl and amino functional groups for attachment via amide bonds to the "A" subunit and a disulfide-containing moiety, respectively.

Thus the "B" and "C" subunits are not particularly limited, and can be, for example, any of the compounds of formulae (V)–(XII), or related compounds disclosed in U.S. Pat. Nos. 5,585,499; 5,475,092; and 5,846,545.

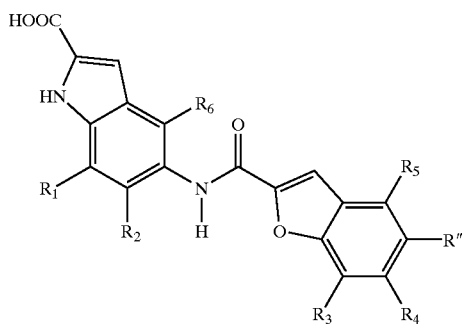

(V)

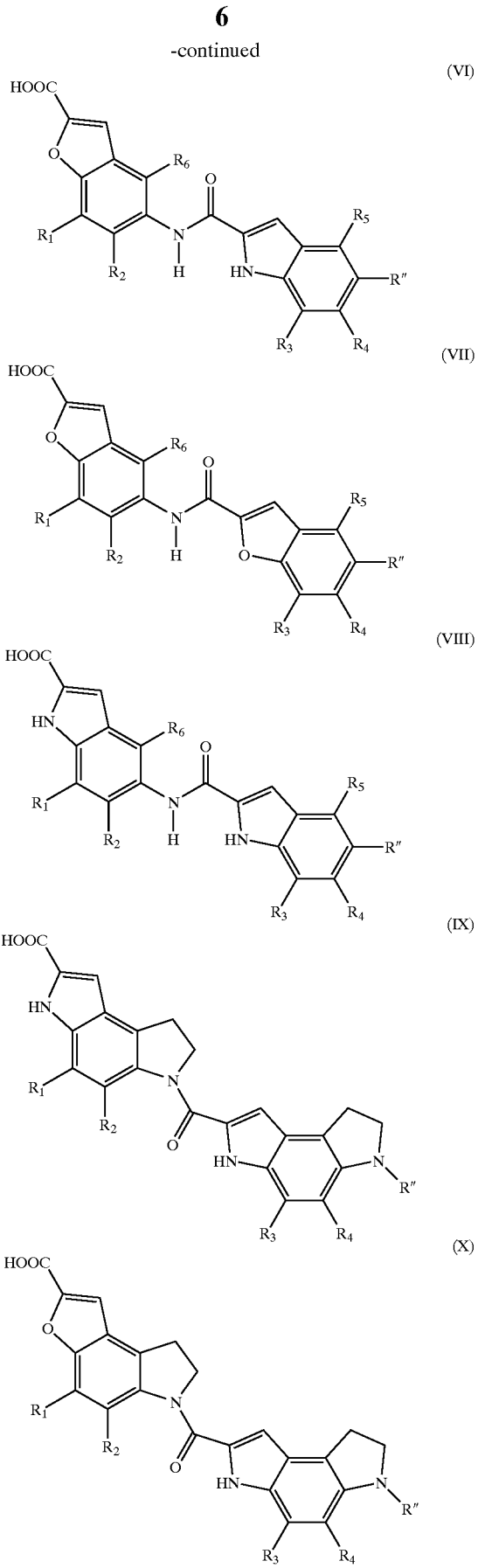

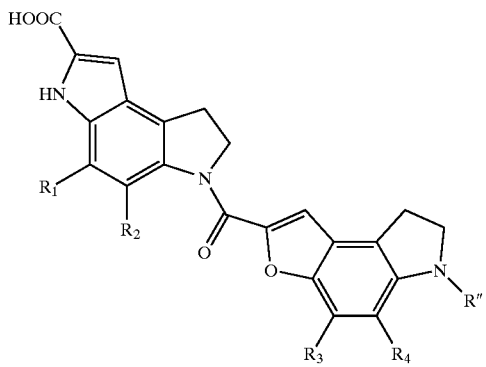

(XI)

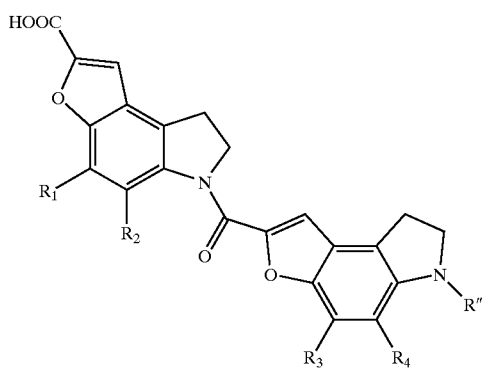

(XII)

Thus, the "B" and "C" subunits of DC1 can include 2-carboxy-indole or 2-carboxy-benzofuran derivatives, or both, as represented by the compounds of formulae (V)–(XII). As may be ascertained from the natural CC-1065 and from the properties of the analogs that have been published (e.g. Warpehoski et al, 31 *J. Med Chem.* 590–603 (1988), Boger at al, 66 *J. Org Chem.* 6654–6661 (2001)), the "B" and "C" subunits can also carry different substituents at different positions on the indole or benzofuran rings, corresponding to positions $R_1$–$R_6$ of formulae (V)–(XII), and retain potent cytotoxic activity.

Within formulae (V)–(XII), $R_1$ to $R_6$, which may be the same or different, independently represent hydrogen, $C_1$–$C_3$ linear alkyl, methoxy, hydroxyl, primary amino, secondary amino, tertiary amino, or amido. Examples of primary amino group-containing substituents are methyl amino, ethyl amino, and isopropyl amino. Examples of secondary amino group-containing substituents are dimethyl amino, diethyl amino, and ethyl-propyl amino. Examples of tertiary amino group-containing substituents are trimethyl amino, triethyl amino, and ethyl-isopropyl-methyl amino. Examples of amido groups include N-methyl-acetamido, N-methyl-propionamido, N-acetamido, and N-propionamido.

Within formulae (V)–(XII), R″ represents an amine or substituted or unsubstituted $C_1$–$C_{20}$ alkyl amine that is capable of forming an amide bond to a carboxyl of the disulfide-containing moiety of DC1. The preferred embodiment of R″ is —$NH_2$.

The disulfide-containing moiety that is used in the synthesis of DC1 is of the structure HOOC—$R_7$—S—$R_8$, wherein $R_7$ represents a linker region that is not particularly limited and can be, for example, a substituted or unsubstituted $C_1$–$C_{20}$ alkyl group, a polyethylene glycol spacer, and the like. Thus, $R_7$ can represent methyl, linear alkyl, branched alkyl, cyclic alkyl, simple or substituted aryl or heterocyclic or a polyethylene glycol chain. Examples of linear alkyls represented by $R_7$ include methyl, ethyl, propyl, butyl, pentyl and hexyl. Examples of branched alkyls represented by $R_7$ include isopropyl, isobutyl, sec.-butyl, tert.-butyl, isopentyl and 1-ethyl-propyl. Examples of cyclic alkyls represented by $R_7$ include cyclopropyl, cyclobutyl, cyclopentyl and cyclohexyl. Examples of simple aryls represented by $R_7$ include phenyl and naphthyl. Examples of substituted aryls represented by $R_7$ include aryls such as phenyl or naphthyl substituted with alkyl groups, with halogens, such as Cl, Br, F, nitro groups, amino groups, sulfonic acid groups, carboxylic acid groups, hydroxy groups and alkoxy groups. Heterocyclics represented by $R_7$ are compounds wherein the heteroatoms are selected from O, N, and S, and examples include furyl, pyrrollyl, pyridyl, (e.g., a 2-substituted pyrimidine group) and thiophene.

$R_8$ represents any suitable thiol leaving group that is capable of undergoing a disulfide exchange reaction whereby DC1 can be attached, for example, to a cell specific reagent such as an antibody or any of the cell binding agents disclosed in U.S. Pat. No. 5,475,092. Preferred embodiments of $R_8$ include —$SCH_3$ and thiopyridyl. Other examples include —Salkyl, —Saryl, glutathione, cysteine and the like.

The term "protecting group" (R) as used herein represents any group that is capable of protecting the amino or phenolic hydroxyl group to which it is attached from further reaction and which is further capable of controlled subsequent removal, for example by treatment with an acid or base. Thus, amino-protecting groups stable to base treatment are selectively removed with acid treatment, and vice versa, and can be used to protect the amino group in the synthesis of seco(-)CBI herein. Examples of such groups are the FMOC (E. Atherton and R. C. Sheppard in The Peptides, S. Udenfriend, J. Meienhofer, Eds., Academic Press, Orlando, 1987, volume 9, p.1), and various substituted sulfonylethyl carbamates exemplified by the Nsc group (Samukov et al., Tetrahedron Lett, 1994, 35:7821; Verhart and Tesser, Rec. Trav. Chim. Pays-Bas, 1987, 107:621). Additional amino-protecting groups include but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), diphenyloxycarbonyl, 2,2,2-trichloroethyl oxycarbonyl, diisopropylmethyl oxycarbonyl, 1-adamantyl oxycarbonyl, vinyl oxycarbonyl, methoxy benzyl oxycarbonyl, nitrobenzyl oxycarbonyl, cyclohexyl oxycarbonyl, cyclopentyl oxycarbonyl, and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Those skilled in the art are familiar with such equivalent amino-protecting groups. As an example, which is not intended to be limiting, amino protecting groups such as 2,6-dinitrobenzenesulfonyl, 4-nitrobenzenesulfonyl or 2,4-dinitrobenzenesulfonyl groups may be used. Alternatively, another amino protecting group may be used instead of a sulfonyl protecting group.

In the present invention, tert-butoxycarbonyl (BOC) is preferred.

The formation of the amide bonds in the synthesis of seco(-)CBI and DC1 can be catalyzed by a variety of agents known to those of skill in the art. For example, carbodiimides are used to mediate the formation of a peptide bond between a carboxylate and an amine, and water soluble and insoluble species of carbodiimide can be selected as appropriate. EDC (1-ethyl-3-(3-dimethylaminopropyl) carbodiimide hydrochloride) is preferred. Other examples of amide coupling reagents useful in the present invention include EDC together with sulfo-NHS, CMC (1-cyclohexyl-3-(2-morpholinoethyl) carbodiimide), DCC (dicyclohexyl carbodiimide), DIC (diisopropyl carbodiimide), Woodward's reagent K, N,N'-carbonyldiimidazole, PyBOP (benzotriazole-1-yl-oxy-tris-pyrrolidinophosphonium heaxflurophosphate), TBTU (2-(1H-Benzotriazole-1-yl)-1,1,3,3-trtramethyluronium tetrafluoroborate), HBTU (2-(1H-Benzotriazole-1-yl)-1,1,3,3-trtramethyluronium hexafluorophosphate), BOP (Benzotriazole-1-yl-oxy-tris-(dimethylamino)-phosphonium hexafluorophosphate), PyBrOP (Bromo-tris-pyrrolidino-phosphonium hexafluorophosphate), and the like.

The isolation of the (−) enantiomer of the diprotected seco(−)CBI precursor, a compound of formula (III), is an important step in the synthesis of seco(−)CBI. Isolation of the (−) enantiomer can be carried out by any method known to those of skill in the art for the separation of enantiomers. For example, the use of a chiral matrix and liquid chromatography is preferred. Most preferably, HPLC over a chiral column is used. It is a benefit of the present invention that the separation of the (−) enantiomer is performed upon the di-protected precursor rather than upon seco(−)CBI (7), as described above. Suitable chiral matrices include, for example, Chiralpak AD column (Diacel), Chiralcel OD, Chiralcel OJ, and the like.

The term "suitable conditions," as applied herein to specific aspects of the synthesis of seco(−)CBI and DC1, such as in reference to alkylation or ring-closure reactions, represents both the specific methods disclosed in the Examples herein and those equivalent methods, suitably adapted to the specific DC1 species that is to be synthesized, known to those of skill in the art.

The synthesis of DC1 requires the coupling, via amide bonds, of seco(−)CBI, a "B" and "C" subunit, and a disulfide-containing moiety. The order in which these components are coupled is not critical and the synthesis can be easily adapted such that the couplings occur in any order. Thus, seco(−)CBI and the "B" and "C" subunits can be first coupled and then the disulfide-containing moiety can be attached, or the disulfide-containing moiety and the "B" and "C" subunits can be first coupled and then the seco(−)CBI can be attached. Both processes are illustrated in the Examples herein.

It is further within the scope of the present invention that the "B" and "C" subunits need not be first coupled via an amide bond in the synthesis of DC1 according to the present invention. Thus, it is within the scope of the present invention that, for example, seco(−)CBI and the "B" subunit are coupled, then the "C" subunit and the disulfide-containing moiety are coupled, and then DC1 is synthesized by coupling through the "B" and "C" subunits. Because DC1 comprises a linear sequence of 4 parts, it will be apparent that many permutations of the synthesis of DC1 according to the present invention are readily attainable.

EXAMPLES

The invention will now be illustrated by reference to certain non-limiting examples. Unless otherwise stated, all percentages, ratios, parts, and the like, are by weight. A summary of the exemplary syntheses (FIGS. 1–3) is followed by a detailed description of each step.

The improved synthesis of CBI exemplified herein (FIG. 1) starts with 1,3-dihydroxy-naphthalene (1). Amination by treatment with ammonia at 125 to 140° C. in a pressure vessel provided 4-hydroxy-2-napthylamine 2, which was then converted to the di-t-boc compound 3 by treatment with di-tert-butyldicarbonate. Iodination with N-iodosuccinimide proceeded in 86% yield to produce 4, which was alkylated to give compound 5 in 93% yield. Ring closure of 5 using tri-butyltin hydride in the presence of 2,2'-azobisisobutyronitrile (AIBN) proceeds smoothly in 94% yield to give the racemic di-t-boc-seco-CBI 6 in 94% yield. Separation of the racemic mixture is readily performed using a chiral HPLC column eluting with 20% isopropanol in hexane, where the retention times of the two isomers differ by 17 minutes, to give the desired di-t-boc-seco (−) CBI isomer 6b. Deprotection with hydrochloric acid provided seco(−)CBI, 7.

Figure 2:
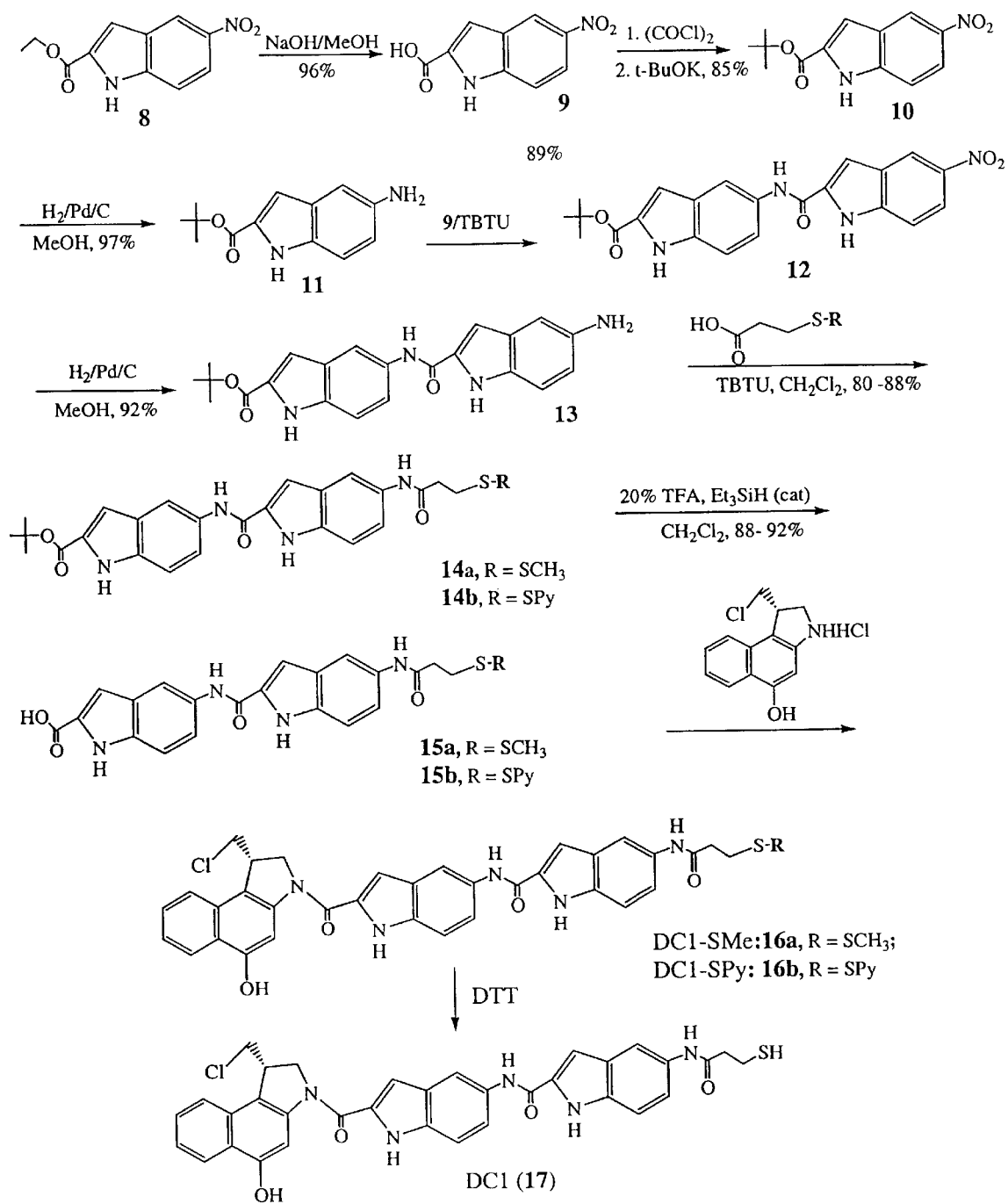
FIG. 2 illustrates an exemplary synthesis (path A) of DC1 according to the method of the present invention.
Figure 3:
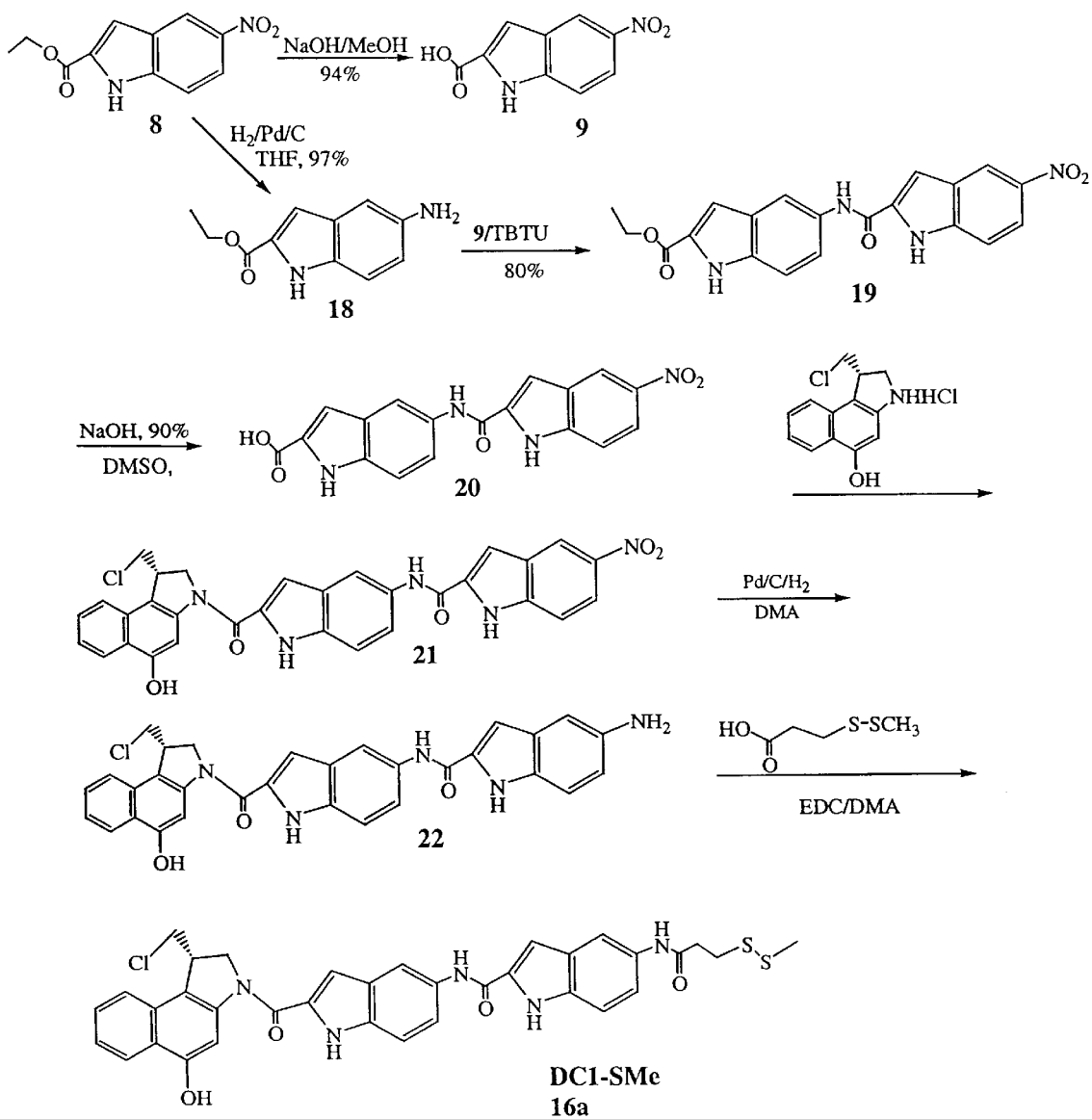
FIG. 3 illustrates a second exemplary synthesis (path B) of DC1 according to the method of the present invention.

Two independent synthetic routes for the conversion of seco-CBI 7 to DC1-SMe 16a are exemplified and are designated Path A (FIG. 2) and Path B (FIG. 3).

In Path A (FIG. 2), the bis-indolyl moiety bearing a disulfide-containing substituent was synthesized, and then coupled in the final step to seco-CBI. In Path B, the bis-indolyl moiety was linked to seco-CBI, and the disulfide-containing substituent was introduced in the final step (FIG. 3).

In Path A, ethyl 5-nitroindole-2-carboxylate (8), which is commercially available, was hydrolyzed to the acid 9, which was then converted into the tert-butyl ester 10. Catalytic reduction of 10 with hydrogen provided the amino ester 11 in quantitative yield. Coupling of 11 with 5-nitroindole-2-carboxylic acid (9) in the presence of O-(benzotriazol-1-yl)-N,N,N',N'-tetramethyluronium tetraflouroborate (TBTU) provided the nitro-bis-indolyl ester 12 in 89% yield. Reduction of the nitro group by catalytic hydrogenation, followed by coupling of the resulting amino compound 13 with 3-(methyldithio)propanoic acid provided 14a. The ester group in 14a was hydrolyzed with trifluoroacetic acid to give carboxylic acid 15a. Coupling of 15a with seco-CBI, in the presence of EDC provided DC1-SMe (16a). Reduction of DC1SMe with dithiothreitol provided DC1 (17).

In Path B, 5-nitroindole-2-carboxylic acid 9 was first condensed with ethyl 5-aminoindole-2-carboxylate 18 to provide the bis-indolyl ester 19. Alkaline hydrolysis of 19, followed by coupling with seco-CBI provided the bis-indolyl-seco-CBI compound 21. Reduction of the nitro group in 21 with hydrogen over Pd/C provided the amino-bis-indolyl-seco-CBI compound 22. Coupling of 22 with 3-(methyldithio)propanoic acid provided DC1-SMe 16a.

Materials and Methtods

Melting points were measured using an Electrothermal apparatus and are uncorrected. NMR spectra were recorded on a Bruker AVANCE400 (400 MHz) spectrometer. Chemical shifts are reported in ppm relative to TMS as an internal standard. Mass spectra were obtained using a Bruker Esquire 3000 system. Ultraviolet spectra were recorded on a Hitachi U1200 spectrophotometer. Analytical HPLC was performed using a Beckman Coulter GOLD 125 system equipped with a Beckman Coulter system GOLD 168 variable wavelength detector and a Chiralcel OD 4.6×250 mm column. Preparative HPLC was performed on a R & S Technology Zonator system equipped with a Hitachi UV detector, using a self-packed Chiralcel OD 7.5×50 cm column. Thin layer chromatography was performed on Analtech GF silica gel TLC plates. Silica gel for flash column chromatography was from Baker. All solvents used were reagent grade or HPLC grade.

Examples 1–5

Synthesis of Seco(−)CBI (5-Hydroxy-3-amino-1-[S]-(chloromethyl)-1,2-dihydro-3H-benz(e)indole) According to the Scheme of FIG. 1.

Example 1

Preparation of N-(tert-Butyloxycarbonyl)-4-O-(tert-butyloxycarbonyl)-2-naphthylamine (3)

A solution of 1,3-dihydroxynaphthalene (1, 50 g, 0.312 mol) in liquid ammonia (200 mL) at −78° C. was sealed in a 1 L steel bomb containing a glass liner. The reaction mixture was warmed to 135±10° C. and 1300 psi for 14 h with vigorous stirring. The vessel was allowed to cool to 60° C., and the ammonia was released slowly. The remaining traces of ammonia were removed by co-evaporation with THF (2×150 mL) under a stream of argon at 60° C. The intermediate 4-hydroxy-2-naphthylamine (2) was not isolated but was immediately converted to the di-tert-butyloxycarbonyl protected compound 3. A solution of di-tert-butyl dicarbonate (175 g, 0.801 mol) in dry THF (300 mL) and N,N-diisopropylethylamine (140 mL, 0.803 mol) were sequentially added to the bomb. The bomb was re-sealed, and the contents were warmed at 100° C. with stirring for 4 h. The bomb was cooled to room temperature, opened, and the residue partitioned between saturated aqueous NaCl (800 mL) and ethyl acetate (500 mL). The aqueous phase was extracted with ethyl acetate (200 mL×2). The combined organic layers were dried (magnesium sulfate), filtered, and concentrated under reduced pressure. Chromatography on silica gel (1:8 to 1:4 ethyl acetate/hexane) and recrystallization with ethyl acetate/ethanol/hexane provided pure 77.41 g (69%) of the title compound (3). $^1$H NMR (CDCl$_3$, 400 MHz) 8.14 (d, 1H, J=8.1 Hz), 7.66 (d, 1H, J=8.1 Hz), 7.43 (dd, 1H, J=6.8, 8.2Hz), 7.35 (dd, 1H, J=6.8, 82 Hz), 7.22 (d, 1H, J=1.8 Hz), 7.15 (br, 1H, NH), 6.69 (s, 1H), 1.59 (s, 9H), 1.37 (s, 9H); $^{13}$C NMR(CDCl$_3$) 153.71, 152.9, 136.11, 135.20, 128.12, 128.01, 126.81, 126.03, 123.61, 107.94, 102.95, 82.98, 82.10, 28.93, 27.69; MS m/z 382.52 (M+Na)$^+$.

Example 2

Preparation of N-(tert-Butyloxycarbonyl)-4-O-(tert-butyloxycarbonyl)-1-iodo-2-naphthylamine (4)

A solution of compound 3 (24.50 g, 68.24 mmol) and N-iodosuccinimide (NIS), (17.70 g, 74.73 mmol) in 250 mL of THF/methanol (1:1) was stirred at −40° C. under argon in the dark for 5 min. Toluenesulfonic acid (0.86 g, 4.52 mmol) was then added, and the reaction mixture was stirred under argon in the dark at −40° C. for 2 h, and then at room temperature for 2 h. The mixture was diluted with ether (800 mL), washed with saturated aqueous NaHCO$_3$ and saturated aqueous NaCl, dried over magnesium sulfate, filtered and concentrated in vacuo. Flash chromatography on silica gel (ethyl acetate/hexane 1:10) was followed by the isolation of the desired product. Crystallization from ethanol/ethyl acetate/hexane afforded 28.46 g (86%) of the title compound 4. Rf=0.48 (10% ethyl acetate/hexane). $^1$H NMR (CDCl$_3$, 400 MHz) 8.27 (d, 1H, J=8.0 Hz), 7.98 (dd, 1H, J=1.5, 8.1 Hz), 7.83 (s, 1H), 7.55 (m, 2H), 7.18 (br, 0.8H, NH), 1.62 (m, 18H); MS m/z 508.36 (M+Na)$^+$.

Example 3

Preparation of 2-[N-(tert-Butyloxycarbonyl)-N-(3-chloro-2-propen-1-yl)amino]-4-O-(tert-butyloxycarbonyloxy)-1-iodonaphthalene (5)

To a solution of compound 4 (940 mg, 1.86 mmol) in 20 mL of dry DMF was added NaH (60% in mineral oil, 150 mg, 3.75 mmol) under an argon atmosphere. After stirring the mixture at 0° C. for 30 min, E, Z-1,3-dichloropropene (1.50 mL, 14.57 mmol) was added. The reaction mixture was stirred at 0° C. under argon for 2 h, then neutralized with 1.0 M NaH$_2$PO$_4$, and extracted with ethyl acetate. The organic layer was dried over magnesium sulfate, filtered and concentrated in vacuo. Flash chromatography on silica gel (ethyl acetate/hexane 1:9) afforded 1.01 g (93%) of the desired compound 5. R$_{fz}$=0.37, R$_{fE}$=0.32 (1:8 ethyl acetate/hexane). (E:Z vinyl chlorides and di-t-boc rotamers). $^1$H NMR (CDCl$_3$, 400 MHz) 8.26 (d, 2H, J=7.7 Hz), 7.96 (m, 2H), 7.59 (br, 4H), 7.20 (s, 1H), 7.16 (s, 1H), 6.17–6.07 (m, 4H), 4H), 4.64 (dd, 1H, J=6.2, 15.2Hz), 4.53 (dd, 1H, J=6.2, 14.7Hz), 4.31 (dd, 1H, J=6.0, 15.0Hz), 3.84 (dd, 1H, J=7.5, 15.0 Hz), 1.58 (S, 9H); 1.33 (s, 9H); $^{13}$C NMR (CDCl$_3$) 153.78, 151.08, 150.98, 133.31, 133.29, 128.66, 128.61, 127.50, 127.41, 126.41, 121.68, 119.03, 84.22, 84.11, 80.99, 77.20, 28.20, 27.66; MS m/z 582.8 (M+Na)$^+$.

Example 4

Preparation of 5-(O-tert-Butyloxycarbonyl)oxy-3-[N-(tert-butyloxycarbonyl)amino-1-(chloromethyl)-1,2-dihydro-3H-benz(e)indole (6)

To a solution of compound 5 (1.36 g, 2.43 mmol) in dry benzene (100 mL) were added tri-n-butyltin hydride (0.70 mL, 2.52 mmol) and 2,2'-azobis(isobutyronitrile) (AIBN) (30 mg, 0.18 mmol). The mixture was stirred under argon at room temperature for 30 min and then refluxed at 80° C. for 2 h. The reaction mixture was cooled, and the solvent was removed in vacuo. Flash chromatography on silica gel (ethyl acetate/hexane 1:9) afforded 1.01 g (94%) of the desired compound 6. R$_f$=0.34 (1:9 ethyl acetate/hexane); $^1$H NMR (CDCl$_3$, 400 MHz) 8.12 (br, 1H), 7.91 (d, 1H, J=8.4 Hz), 7.69 (d, 1H, J=8.4 Hz), 7.50 (dt, 1H, J=1.0, 6.9, 7.0 Hz), 7.37 (dt, 1H, J=0.9, 6.9, 6.9 Hz), 4.27 (br, 1H), 4.12 (t, 1H, J=9.0+10.0 Hz), 3.99 (m, 1H), 3.90 (dd, 1H, J=2.4, 11.0 Hz), 3.45 (t, 1H, J=10.8+10.8 Hz), 1.58 (S, 18H); $^{13}$C NMR (CDCl$_3$) 152.27, 151.84, 147.99, 130.17, 127.62, 124.33, 122.46, 122.22, 108.95, 83.78, 52.80, 46.13, 28.36, 27.79; MS m/z 456.9 (M+Na)$^+$.

Resolution of (6): The enantiomeric mixture of compound 6 (1.0 g in 20 mL of ethyl acetate) was resolved on an HPLC preparative column (20 mm, 7.5×50 cm, packed with Diacel Chiralcel OD) using 15% isopropanol-hexane eluant (180 mL/min). The two enantiomers eluted with retention times of 18.5 minutes [6a (+) enantiomer] and 35.8 minutes [6b (−) natural (1S) enantiomer]. 6b (−)-(1S): [α]$^{25}$=−49.6° (c=5.25 CHCl$_3$).

Example 5

Preparation of 5-Hydroxy-3-amino-1-[S]-(chloromethyl)-1,2-dihydro-3H-benz(e)indole (7)

To a solution of 6b (100 mg, 0.25 mmol) in 5 mL of ethyl acetate, was added conc. HCl (0.2 mL) and triethylsilane (0.2 mL). After stirring for 3 h under argon, the mixture was diluted with 10 mL of 1:1 dichloromethane/toluene and evaporated to dryness. The dry solid was co-evaporated three times with dichloromethane/toluene and then immediately used for coupling to di-indole compounds without further purification, (~90% pure), MS m/z 234.78 (M+H)$^+$.

Examples 6–15

Exemplary Synthesis of DC1 According to the Scheme of Path A (FIG. 2)

Example 6

Preparation of tert-Butyl 5-Nitroindole-2-carboxylate (10)

To a stirred solution of ethyl-5-nitroindole-2-carboxylate (8) (25.0 g, 106.8 mmol), in 500 mL of THF-methanol (1:1, v/v) at room temperature, was added a solution of NaOH (40 g, 1.0 mmol) in 300 mL of water. The resulting deep red-brown solution was stirred for 3 h, then quenched by acidification to pH 1 with dilute HCl. The precipitated product was collected by vacuum filtration, and the remaining dissolved product was extracted with THF/ethyl acetate (1:2, v/v, 2×400 mL). The precipitate was dissolved in THF and this solution was combined with the organic layers from the extractions, supra. Drying over magnesium sulfate, filtration, concentration in vacuo, and crystallization of the residue from THF/ethyl acetate/hexane afforded 21.1 g (96% yield) of 5-nitroindole-2-carboxylic acid (9). $^1$H NMR (DMSO), 11.50 (s, 1H), 7.20 (d, 1H, J=8.4 Hz), 6.85 (s, 1H), 6.70 (m, 2H).

To a stirred solution of 9 (12.8 g, 61.2 mmol) in dry THF (200 mL) under argon was added oxalyl chloride (12.0 mL, 137.5 mmol) followed by DMF (0.1 mL), which caused a vigorous evolution of gas. After 40 min, the reaction mixture was evaporated to dryness. The resulting solid was re-dissolved in THF (150 mL), cooled to ~30° C., and stirred under argon. A solution of potassium t-butoxide (1.0 M in THF, 140 mL, 140 mmol) was then added dropwise over 45 min, and stirring was continued for an additional 45 min. The reaction was quenched with 600 mL of water, neutralized with few drops of a 10% aqueous solution of $H_3PO_4$ and extracted with ethyl acetate (3×400 mL). The organic extracts were washed with saturated aqueous $NaHCO_3$, water, and then dried over magnesium sulfate, filtered, concentrated and crystallized with ethanol/hexane to afford compound 10 (9.62 g, 85% yield). $R_f$=0.35 (1:5 Ethyl acetate/Hexane); $^1$H NMR (CDCl$_3$), 11.63 (s, 1H), 8.66 (dd, 1H, J=0.5, 1.3Hz), 8.20 (dd, 1H, J=0.5, 9.0 Hz), 7.48 (dd, 1H, J=0.5, 9.1 Hz), 7.28 (dd, 1H, J=0.9, 11.1 Hz), 1.63 (s, 9H); $^{13}$C NMR 160.39, 142.12, 138.11, 132.10, 126.78, 120.22, 119.83, 111.98, 109.82, 82.91, 28.26; MS m/z 285.43 (M+Na)$^+$.

Example 7

Preparation of tert-Butyl 5-Aminoindole-2-carboxylate (11)

A 500 mL Par hydrogenation bottle was charged with compound 10 (5.80 g, 22.14 mmol), 10% Pd/C (0.6 g) and methanol/THF (150 mL, 1:4 v/v), and purged with hydrogen. The reaction mixture was shaken with 50 psi H$_2$ over night. The catalyst was removed by filtration and the solvent was evaporated to give 4.98 g (97% yield) of the title compound 11 as brown solid. $^1$H NMR (DMSO), 11.42 (s, 1H), 7.18 (d, 1H, J=8.3 Hz), 6.83 (s, 1H), 6.71 (s, 1H), 6.67 (d, 1H, J=8.4 Hz), 1.62 (s, 9H). This product is unstable and therefore it was immediately used in the following step.

Example 8

Preparation of tert-Butyl 5-(5'-Nitroindol-2'-yl-carbonyl Amino)indole-2-carboxylate (12)

To a mixture of compounds 9 (4.70 g, 22.81 mmol) and 11 (5.20 g, 22.41 mmol) in DMF (200 mL) were added under argon O-(benzotriazol-1-yl)-N, N',N'-tetramethyluronium tetraflouroborate (TBTU, 10.5 g, 32.70 mmol) and diisopropylethylamine (DIPEA, 8.0 mL, 45.83 mmol). The reaction mixture was stirred overnight. The mixture was concentrated and then suspended in ethyl acetate and aqueous NaHCO$_3$ (satd.). The solid compound was filtered, washed with water, and then re-suspended with aqueous 1 M NaH$_2$PO$_4$, pH 3.0, filtered, and washed again with water. The solid was then dried under vacuum to yield 12 (8.40 g, 89% yield). $R_f$=0.31 (1:2 THF/hexane); $^1$H NMR (DMSO), 12.43 (s, 1H), 11.69 (s, 1H), 10.41 (s, 1H), 8.77 (d, 1H, J=2.2 Hz), 8.13 (dd, 2H, J=2.3, 9.0 Hz), 7.64 (t, 2H, J=9.2 Hz), 7.47 (d, 1H, J=8.9 Hz), 7.08 (s, 1H), 1.59 (s, 9H); $^{13}$C NMR (DMSO), 161.48, 159.53, 142.19, 140.38, 136.30, 135.27, 132.28, 130.30, 127.43, 127.25, 120.57, 120.12, 114.08, 113.74, 108.22, 106.64, 81.74, 28.84; MS m/z 443.85 (M+Na)$^+$.

Example 9

Preparation of tert-Butyl 5-(5'-Aminoindol-2'-yl-carbonyl Amino)indole-2-carboxylate (13)

A 250 mL Parr hydrogenation bottle was charged with compound 12 (2.40 g, 5.71 mmol), 10% Pd/C (0.3 g), and DMA (50 mL), and purged with hydrogen. The reaction mixture was shaken with 40 psi H$_2$ over night. The catalyst was removed by filtration and the solvent was evaporated to give 2.05 g (92% yield) of the title compound 13 as a brown solid. $^1$H NMR (DMSO), 11.75, (s, 1H), 11.67 (s, 1H), 10.17 (s, 1H), 8.10 (d, 1H, J=1.2 Hz), 7.59 (t, 2H, J=8.8 Hz), 7.45 (m, 1H), 7.35 (m, 1H), 7.17 (dd, 1H, J=0.8, 8.0 Hz), 7.06 (d, 1H, J=2.0 Hz), 1.57 (s, 9H); MS m/z 390.72 (M+Na)$^+$. This product is unstable and therefore it was used immediately in the following step.

Example 10

Preparation of tert-Butyl 5-[5'-(3"-Methyldithiopropionyl)indol-2'-yl-carbonyl Amino] indole-2-carboxylate (14a)

To a solution of 13 (2.0 g, 5.12 mmol)) in DMA (30 mL) was added of 3-(methyldithio)propionic acid (0.90 g, 5.92 mmol), EDC (3.0 g, 15.33 mmol) and DIPEA (0.90 mL, 5.12 mmol). The reaction mixture was stirred over night under argon, and then diluted with 70 mL of 1.0 M NaH$_2$PO$_4$, pH 6.0 and extracted with THF/ethyl acetate (1:1, 4×70 mL). The organic layers were combined, dried over magnesium sulfate, filtered and evaporated. The residue was purified by silica gel chromatography (1:3 acetone/toluene) and crystallized from THF/hexane to yield compound 14a (2.30 g, 86% yield). Mp=279–283° C. (dec), $R_f$=0.31 (1:3 THF/toluene); $^1$H NMR (CD$_3$COCD$_3$), 10.75 (d, 2H, J=3.07 Hz), 9.50 (s, 1H), 9.14 (s, 1H), 8.20 (d, 1H, J=2.0 Hz), 8.14 (d, 1H, J=1.8 Hz), 7.62 (dd, 1H, J=2.0, 8.9 Hz), 7.46 (dd, 2H, J=0.7, 8.1 Hz), 7.34 (dd, 1H, J=2.0, 10.8 Hz), 7.26 (d, 1H, J=1.5 Hz), 7.07 (dd, 1H, J=0.9, 2.1 Hz), 3.05 (t, 2H, J=7.1 Hz), 2.76 (t, 2H, J=7.0 Hz), 2.42 (s, 3H), 1.57 (s, 9H); $^{13}$C NMR 169.42, 161.58, 160.32, 135.31, 134.76, 133.56, 133.40, 133.12, 130.86, 128.72, 128.27, 120.27, 118.75, 113.69, 113.09, 113.02, 112.69, 108.27, 103.58, 81.66, 37.28, 34.00, 28.41; MS m/z 547.88 (M+Na)$^+$.

Example 11

Preparation of 5-[5'-(3"-Methyldithiopropionyl) indol-2'-yl-carbonyl Amino]indole-2-carboxylic Acid (15a)

A mixture of compound 14a (300 mg, 0.57 mol) and Et$_3$SiH (1.5 mL) in dichloromethane (30 mL) was stirred under argon. Trifluoroacetic acid (7.0 mL) was added and the mixture was stirred for 3 h, and then diluted with toluene (25 mL). The mixture was evaporated to dryness and crystallized with THF/toluene/hexane to yield compound 15a (245 mg, 92% yield). $^1$H NMR (DMSO), 11.71 (s, 1H), 11.61 (s, 1H), 10.10 (s, 1H), 9.92 (s, 1H), 8.11 (d, 1H, J=1.9 Hz), 8.02 (d, J=1.7 Hz), 7.55 (dd, 1H, 2.0, 11.0 Hz), 7.42 (d, 1H, J=8.8 Hz), 7.39 (d, 1H, J=8.8 Hz), 7.34 (d, 1H, J=2.0 Hz), 7.31 (dd, 1H, J=2.0, 8.8 Hz), 7.08 (d, 1H, J=1.3 Hz), 3.06 (t, 2H, J=7.0 Hz), 2.75 (t, 2H, J=7.0 Hz), 2.45 (s, 3H); $^{13}$C NMR (DMSO), 168.70, 162.79, 159.47, 134.37, 133.56, 132.44, 131.98, 131.64, 126.96, 126.75, 119.62, 117.74, 113.04, 112.46, 112.35, 111.44, 107.36, 103.37, 36.03, 33.01; MS 490.81 (M+Na)$^+$.

Example 12

Preparation of (S)-N-[2-{(1-Chloromethyl)-1,2-dihydro-5-hydroxy-3H-benz(e)indol-3-yl}carbonyl]-1H-indol-5-yl]-5-[(3-methyldithio-1-oxopropyl)amino]-1H-indole-2-carboxamide (16a) (DC1SMe)

To a solution of compounds 7 (55 mg, 0.20 mmol) and 15a (100 mg, 0.21 mmol) in DMA (7.0 mL) was added EDC (120 mg, 0.62 mmol) under argon. The reaction mixture was stirred overnight, then a few drops of 50% acetic acid were added, and the mixture was evaporated to dryness. The residue was purified by column chromatography over silica gel (20% to 30% acetone in toluene) and crystallized with THF/toluene/hexane to afford DC1SMe (16a) (108 mg, 79% yield). $R_f$=0.40 (3:7 acetone/toluene); $^1$H NMR (CD$_3$COCD$_3$) 10.91 (s, 1H), 10.88 (s, 1H), 9.64 (s, 1H), 9.56 (s, 1H), 9.27 (s, 1H), 8.35 (d, 1H, J=1.9 Hz), 8.25 (d, 1H, J=8.0 Hz), 8.17 (d, 1H, J=1.9 Hz), 8.07 (s, 1H), 7.88 (d, 1H, J=8.3 Hz), 7.64 (dd, 1H, J=2.0, 8.1 Hz), 7.58–7.50 (m, 3H), 7.38–7.35 (m, 2H), 7.31 (d, 1H, J=1.7 Hz), 7.26 (d, 1H, J=1.7 Hz), 4.86 (dd, 1H, J=8.7, 11.0 Hz), 4.80 (dd, 1H, J=2.3, 10.9 Hz), 4.30 (m, 1H), 4.07 (dd, 1H, J=3.1, 11.0 Hz), 3.83 (dd, 1H, J=8.4, 11.2 Hz), 3.09 (t, 2H, J=7.1 Hz), 2.83 (t, 2H, J=7.1 Hz), 2.45 (s, 3H); $^{13}$C NMR 169.56, 161.10, 160.43, 155.13, 143.50, 134.78, 134.46, 133.55, 133.34, 133.03, 132.57, 131.21, 128.80, 128.69, 128.21, 124.22, 124.02, 123.53, 123.44, 120.16, 118.79, 116.45, 113.91113.02, 112.95, 112.73, 106.78, 103.72, 101.63, 56.01, 47.73, 43.10, 37.25, 34.01, 23.00; MS m/z 706.71 (M+Na)$^+$, 708.58, 707.71, 722.34 (M+K)$^+$, 724.42.

Example 13

Preparation of tert-Butyl 5-[5'-(3''-(2-Pyridyldithio)propionyl)indol-2'-yl-carbonyl Amino]indole-2-carboxylate (14b)

To a solution of compound 13 (1.00 g, 2.56 mmol) in DMA (15 mL) was added of 3-(2-pyridyldithio)propionic acid (0.475 g, 2.21 mmol), EDC (1.26 g, 6.56 mmol), and DIPEA (0.20 mL). After stirring under argon overnight, the mixture was diluted with 70 mL of 1.0 M NaH$_2$PO$_4$, pH 3.0 and extracted with THF/ethyl acetate (1:1, 4×60 mL). The organic layers were combined, dried over magnesium sulfate, filtered, evaporated, and purified by silica gel chromatography (1:5 THF/dichloromethane). The product was isolated and recrystallized with THF/ethyl acetate/hexane to yield 1.13 g (87% yield) of the title compound 14b. Mp=285–290 (dec), $R_f$=0.31 (1:5 THF/toluene); $^1$H NMR (CD$_3$COCD$_3$), 10.78 (d, 2H, J=14.3 Hz), 9.52 (s, 1H), 9.23 (s, 1H), 8.45 (dd, 1H, J=0.9, 4.8 Hz), 8.23 (d, 1H, J=1.9 Hz), 8.17 (d, 1H, J=1.8 Hz), 7.84 (dd, 1H, J=1.0, 8.1 Hz), 7.78 (m, 1H), 7.64 (dd, 1H, J=2.1, 8.9 Hz), 7.49 (t, 2H, J=8.8 Hz), 7.35 (dd, 1H, J=2.0, 8.9 Hz), 7.29 (d, 1H, J=1.5 Hz), 7.25 (m, 1H), 7.10 (dd, 1H, J=0.8, 2.1 Hz), 3.21 (t, 2H, J=7.0 Hz), 2.85 (t, 2H, J=7.0 Hz), 1.60 (s, 9H); $^{13}$C NMR 169.15, 161.57, 160.86, 150.44, 138.22, 135.30, 134.78, 133.58, 133.13, 130.86, 128.27, 125.75, 121.73, 120.26, 120.05, 118.75, 113.68, 113.09, 113.03, 112.70, 108.26, 103.56, 81.64, 36.74, 35.25, 28.41; MS m/z 610.48 (M+Na)$^+$, 626.56 (M+K)$^+$.

Example 14

Preparation of 5-[5'-(3''-(2-Pyridyldithio)propionyl)indol-2'-yl-carbonyl Amino]indole-2-carboxylic Acid (15b)

A mixture of compound 14b (115 mg, 0.195 mol) and Et$_3$SiH (0.30 mL) in dichloromethane (4.0 mL) was stirred to under argon. To the milky mixture was added trifluoroacetic acid (1.0 mL), and the mixture became clear. After stirring for 2 hrs, the reaction mixture was diluted with 5 mL of toluene. The mixture was evaporated to dryness and crystallized with THF/toluene/hexane to yield of 93 mg (90% yield) of compound 15b. $^1$H NMR (DMSO), 12.92 (br, 0.7H), 11.74 (s, 1H), 11.63 (s, 1H), 10.11 (s, 1H), 9.92 (s, 1H), 8.47 (dd, 1H, J=0.9, 4.6 Hz), 8.13 (s, 1H), 8.02 (s, 1H), 7.81 (m, 2H), 7.56 (d, 1H, J=9.0 Hz), 7.41 (m, 2H), 7.34 (s, 1H), 7.28–7.21 (m, 2H), 7.10 (s, 1H), 3.15 (t, 2H, J=7.0 Hz), 2.77 (t, 2H, J=6.9 Hz); $^{13}$C NMR 168.34, 162.70, 159.42, 159.16, 149.61, 137.80, 134.34, 133.53, 132.41, 131.88, 131.63, 128.96, 126.90, 126.69, 121.18, 119.60, 119.19, 112.98, 112.42, 112.31, 111.42, 107.47, 35.53, 33.97; MS m/z 532.31, (M+H)$^+$, 553.41, 554.52 (M+Na)$^+$;

Example 15

Preparation of (S)-N-[2-{(1-Chloromethyl)-1,2-dihydro-5-hydroxy-3H-benz(e)indol-3-yl}carbonyl]-1H-indol-5-yl]-5-[(3-pyridyldithio-1-oxopropyl)amino]-1H-indole-2-carboxamide, DC1SPy (16b)

To a solution of compounds 7 (25 mg, 0.094 mmol) and 15b (50 mg, 0.094 mmol) in 10 mL of DMA was added EDC (120 mg, 0.62 mmol) under argon. After stirring overnight, a few drops of 50% acetic acid and toluene (5 mL) were added, the mixture was evaporated to dryness, and the residue was purified by silica gel chromatography (30% acetone in toluene). The product was isolated and recrystallized from THF/toluene/hexane to afford 48 mg (68% yield) of the title compound 16b. MS m/z 769.43 (M+Na)$^+$, 771.51, 785.62 (M+K)$^+$.

Examples 16–20

Exemplary Synthesis of DC1 According to the Scheme of Path B (FIG. 3)

Example 16

Preparation of Ethyl 5-Aminoindole-2-carboxylate (18)

A 500 mL Par hydrogenation bottle was charged with ethyl 5-nitroindole-2-carboxylate (8) (5.0 g, 21.36 mmol), 10% Pd/C (0.3 g), methanol/THF (150 mL, 1:4 v/v), and was purged with hydrogen. The reaction mixture was shaken with 40 psi H$_2$ overnight. The catalyst was removed by filtration and the solvent was evaporated to give 4.10 g (94% yield) of the title compound 18 as a brown solid. $^1$H NMR (CDCl$_3$), 8.77 (s, 1H), 7.26 (s, 1H), 7.23 (t, 1H, J=0.8 Hz), 7.21 (d, 1H, J=0.7 Hz), 7.03 (dd, 1H, J=0.7, 1.5 Hz), 6.93 (dd, 1H, J=0.7, 1.6 Hz), 6.80 (dd, 1H, J=2.2, 8.6 Hz), 4.38 (dd, 2H, J=7.2, 14.3 Hz), 1.40 (t, 3H, J=7.2 Hz); $^{13}$C NMR (CDCl$_3$) 162.02, 140.30, 138.14, 131.87, 128.45, 127.77, 117.12, 112.50, 107.36, 105.86, 60.87, 14.41. This product is unstable and therefor it was used immediately in next step.

Example 17

Preparation of Ethyl 5-(5'-Nitroindol-2'-yl-carbonyl Amino)indole-2-carboxylate (19)

To a mixture of compounds 9 (1.020 g, 5.00 mmol) and 18 (1.02 g, 4.95 mmol) in DMF (30 mL) was added TBTU (4.0 g, 12.40 mmol) and DIPEA (1.8 mL) under argon. The reaction mixture was stirred overnight. After concentration, the mixture was diluted with ethyl acetate (30 mL) and saturated NaHCO$_3$ (150 mL), and the solid was suspended between the two layers. The solid compound was filtered, washed with water and then re-suspended with 1 M NaH$_2$PO$_4$, pH 3.0, filtered, and washed with water again. The product was dried under vacuum to provide compound 19 (1.543 g, 79% yield). R$_f$=0.31 (1:2 THF/hexane); $^1$H NMR (DMSO), 12.45 (s, 1H), 11.90 (s, 1H), 10.43 (s, 1H), 8.77 (d, 1H, J=1.9 Hz), 8.15 (s, 1H), 8.13 (dd, 1H, J=2.2, 9.1 Hz), 7.70 (s, 1H), 7.61 (m, 2H), 7.46 (d, 1H, J=8.9 Hz), 7.18 (s, 1H), 4.35 (dd, 2H, J=7.1, 14.1 Hz), 1.35 (t, 3H, J=7.1 Hz); $^{13}$C NMR (DMSO), 161.22, 158.68, 141.32, 139.50, 135.37, 134.60, 131.47, 128.01, 126.56, 126.38, 119.92, 119.27, 118.59, 113.27, 112.87, 112.60, 107.77, 105.69, 60.43, 14.31; MS m/z 443.85 (M+Na)$^+$.

Example 18

Preparation of 5-(5'-Nitroindol-2'-yl-carbonyl Amino)indole-2-carboxylic Acid (20)

To a solution of compound 19 (630 mg, 1.60 mmol) in DMSO (15 mL) was added NaOH (1.0 g) in 5.0 mL of H$_2$O. After stirring for 1 h, the mixture was concentrated and co-evaporated three time with 10 mL of H$_2$O at 60° C. under reduced pressure. The residual solution was diluted with cold methanol and H$_2$O, yielding a solid. The solid compound was filtered and dried under vacuum to give compound 20 (530 mg, 90% yield). $^1$H NMR (DMSO), 12.48 (s, 1H), 11.75 (s, 1H), 10.44 (s, 1H), 8.77 (s, 1H), 8.15 (s, 1H), 8.10 (d, 1H, J=9.3 Hz), 7.69 (s, 1H), 7.60 (m, 2H), 7.44 (d, 1H, J=8.9 Hz), 7.10 (s, 1H); $^{13}$C NMR (DMSO), 161.91, 158.66, 141.32, 139.52,135.45, 134.44, 131.26, 128.01, 126.72, 126.39, 119.47, 119.25, 118.02, 113.24, 112.88, 112.48, 107.23, 105.71; MS m/z 386.66 387.85 (M+Na)$^+$.

Example 19

Preparation of 1-[S]-(Chloromethyl)-5-hydroxy-3-{{5-[5'-nitroindol-2'-yl-carbonyl Amino]indole-2-yl}carbonyl}-1,2-dihydro-3H-benz[e]indole (21)

To a solution of compounds 7 (20 mg, 0.072 mmol) and 20 (25 mg, 0.068 mmol) in DMA (3.0 mL) was added EDC (40 mg, 0.20 mmol) under argon. The reaction mixture was stirred overnight, a few drops of 50% acetic acid was added, and the mixture was evaporated to dryness. The residue was purified by preparative TLC on silica (40% acetone in toluene) to afford 25 mg of compound 21. $^1$H NMR (DMF-d$_7$) 12.54 (s, 1H), 11.73 (s, 1H), 10.60 (s, 1H), 10.58 (s, 1H), 8.80 (d, 1H, J=2.3 Hz), 8.42 (d, 1H, J=1.9 Hz), 8.25 (d, 1H, J=8.5 Hz), 8.19 (dd, 1H, J=2.1, 9.1 Hz), 8.09 (br, 1H), 7.95 (d, 1H, J=8.3 Hz), 7.82 (d, 1H, J=1.5 Hz), 7.79 (d, 1H, J=9.1 Hz), 7.74 (dd, 1H, J=2.0, 8.9 Hz), 7.62 (d, 1H, J=8.8 Hz), 7.58 (dt, 1H, J=1.7, 7.0+7.0 Hz), 7.42 (dt, 1H, J=1.2, 7.0+7.0 Hz), 7.33 (d, 1H, J=1.7 Hz), 4.91 (t, 1H, J=11.0 Hz), 4.77 (dd, 1H, J=2.1, 11.1 Hz), 4.33 (m, 1H), 4.13 (dd, 1H, J=3.1, 11.1 Hz), 3.97 (dd, 1H, J=7.9, 11.1 Hz); $^{13}$C NMR 163.35, 161.48, 160.05, 155.79, 142.98, 137.18, 135.03, 133.22, 133.16, 131.50, 128.85, 128.45, 128.11, 124.62, 124.02, 123.76, 120.33, 119.36, 118.70, 116.45, 114.00, 113.08, 106.97, 105.02, 101.53; MS m/z 602.96 (M+Na)$^+$, 604.78, 603.81, 618.64 (M+K)$^+$, 620.48.

Example 20

Preparation of (S)-N-[2-{(1-Chloromethyl)-1,2-dihydro-5-hydroxy-3H-benz(e)indol-3-yl}carbonyl]-1H-indol-5-yl]-5-[(3-methyldithio-1-oxopropyl)amino]-1H-indole-2-carboxamide (16a) (DC1-SMe)

A solution of compound 21 (10 mg, 0.017 mmol) in DMA (2.5 mL) was treated with Pd/C (10 mg), 5 µl of HCl (conc.) and DMA (2.5 mL). After the air was removed evacuated, hydrogen was introduced via a hydrogen balloon overnight. The catalyst was removed by filtration and the solvent was evaporated to give compound 22 as a brown solid. The solid compound was used directly without further purification.

To a solution of compound 22 in DMA (2 mL) under argon was added 3-(methyldithio)propionic acid (5 mg, 0.032 mmol) and of EDC (15 mg, 0.078 mmol). After stirring overnight, two drops of 50% acetic acid were added to the mixture and the mixture was evaporated to dryness. The residue was purified by preparative silica gel chromatography (40% acetone in toluene) to afford 6 mg of DC1-SMe (16b). MS m/z 706.66 (M+Na)$^+$, 708.79, 707.86; $^1$H NMR data is the same as above DC1.

Certain patents and printed publications have been referred to in the present disclosure, the teachings of which are hereby each incorporated in their respective entireties by reference.

While the invention has been described in detail and with reference to specific embodiments thereof, it will be apparent to one of skill in the art that various changes and modifications can be made thereto without departing from the spirit and scope thereof.

What is claimed is:

1. The compound of formula (II):

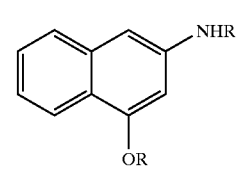

(II)

wherein R is a protecting group selected from the group consisting of tert-butyloxycarbonyl, diphenyloxycarbonyl, fluorenylmethyl oxycarbonyl, 2,2,2-trichloroethyl oxycarbonyl, 2-trimethylsilylethyl oxycarbonyl, diisopropylmethyl oxycarbonyl, 1-adamantyl oxycarbonyl, vinyl oxycarbonyl, allyl oxycarbonyl, benzyl oxycarbonyl, methoxy benzyl oxycarbonyl, nitrobenzyl oxycarbonyl, cyclohexyl oxycarbonyl, cyclopentyl oxycarbonyl.

2. The compound of claim 1, wherein R is tert-butyloxycarbonyl.

\* \* \* \* \*